US010668439B2

(12) United States Patent
Le Saux et al.

(10) Patent No.: US 10,668,439 B2
(45) Date of Patent: Jun. 2, 2020

(54) CULTURE MEDIUM PREPARATOR COMPRISING A VESSEL PROVIDED WITH A CENTRAL STIRRER PUT INTO ROTATION BY A MAGNETIC RING

(71) Applicant: Alliance Bio Expertise, Guipry (FR)

(72) Inventors: Philippe Le Saux, Blain (FR); Morgan Gilet, Caulnes (FR)

(73) Assignee: ALLIANCE BIO EXPERTISE, Guipry (FR)

( * ) Notice: Subject to any disclaimer, the term of this patent is extended or adjusted under 35 U.S.C. 154(b) by 155 days.

(21) Appl. No.: 15/782,347

(22) Filed: Oct. 12, 2017

(65) Prior Publication Data

US 2018/0099255 A1  Apr. 12, 2018

(30) Foreign Application Priority Data

Oct. 12, 2016 (FR) ...................................... 16 59865

(51) Int. Cl.
*B01F 13/00* (2006.01)
*B01F 13/08* (2006.01)
(Continued)

(52) U.S. Cl.
CPC ...... *B01F 13/0827* (2013.01); *B01F 13/0863* (2013.01); *C12M 23/02* (2013.01);
(Continued)

(58) Field of Classification Search
CPC . B01F 13/0827; B01F 13/0863; C12M 23/02; C12M 99/00; C12M 27/00
See application file for complete search history.

(56) References Cited

U.S. PATENT DOCUMENTS

2006/0092761 A1* 5/2006 Terentiev ................ B01F 7/162
366/274
2008/0248552 A1* 10/2008 Castillo Fernandez ......................
B01F 7/1635
435/243

FOREIGN PATENT DOCUMENTS

| EP | 0257750 A2 | 3/1988 |
| EP | 0259002 A2 | 3/1988 |
| WO | 9406553 A1 | 3/1994 |

OTHER PUBLICATIONS

English Translation of the French Written Opinion dated Jul. 4, 2017 for corresponding French Application No. 1659865, filed Oct. 12, 2016.

(Continued)

*Primary Examiner* — Anshu Bhatia
(74) *Attorney, Agent, or Firm* — David D. Brush; Westman, Champlin & Koehler, P.A.

(57) ABSTRACT

A culture medium preparator includes a cylindrical vessel that terminates at the low part in a substantially hemispherical cap, a lid and a stirrer placed in the vessel. The stirrer includes a vertical tube placed in the center of the vessel, a plurality of blades put into rotation about the tube and magnetic masses at the periphery so that they are placed in proximity to the internal wall of the vessel. The preparator furthermore includes a magnetic ring in rotation about the internal wall at the same height as the magnetic masses. The magnets attract the magnetic masses, the magnetic ring being moved in rotation by a motor. In this way, the stirrer is driven in rotation without requiring mechanical elements placed inside the vessel, the absence of such elements facilitating the cleaning.

6 Claims, 5 Drawing Sheets

Figure 1:
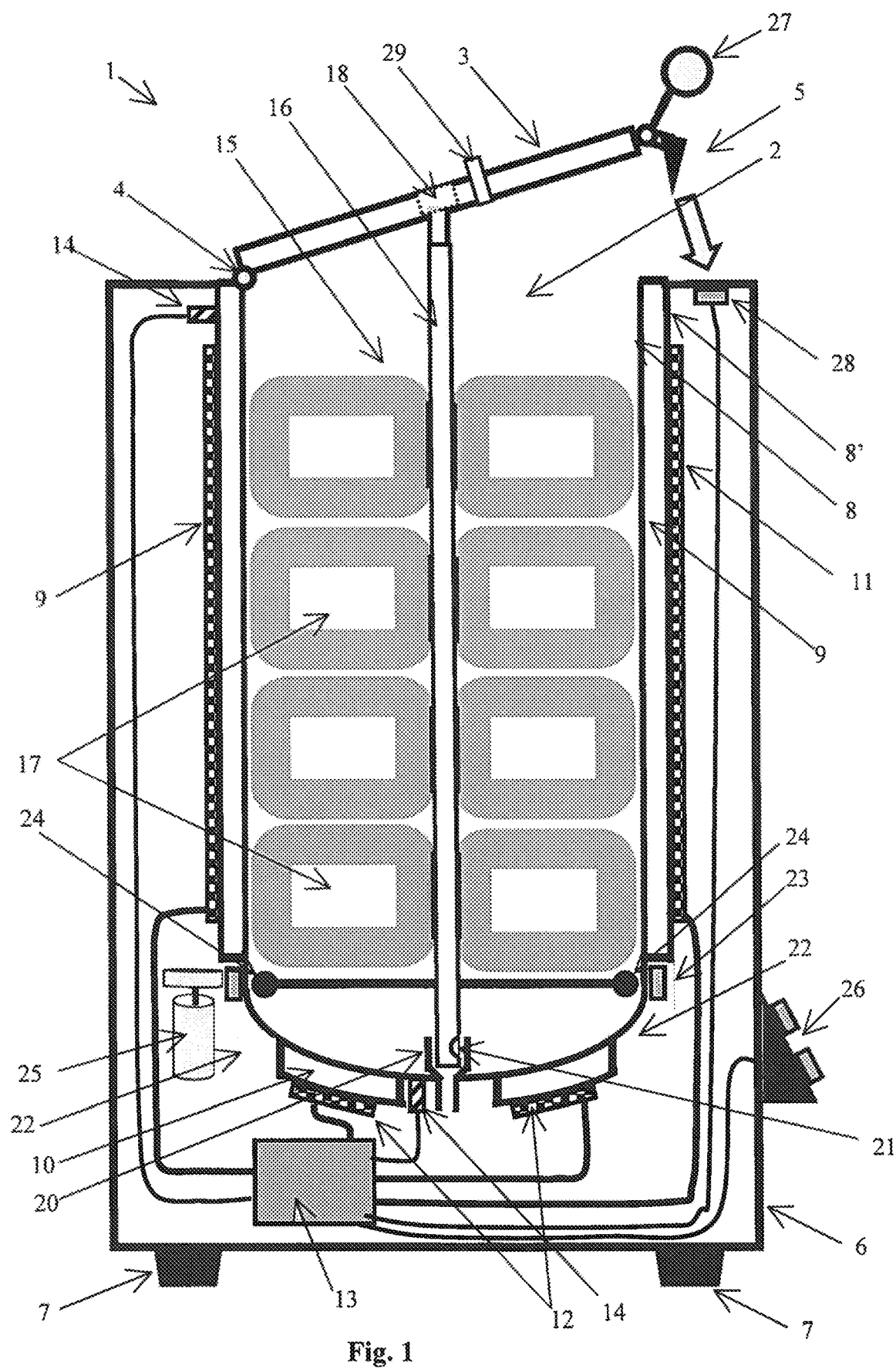

(51) Int. Cl.
*C12M 1/00* (2006.01)
*C12M 1/06* (2006.01)
*C12M 1/02* (2006.01)

(52) U.S. Cl.
CPC ............ *C12M 27/02* (2013.01); *C12M 99/00* (2013.01); *C12M 27/00* (2013.01)

(56) References Cited

OTHER PUBLICATIONS

French Search Report and Written Opinion dated Jul. 4, 2017 for corresponding French Application No. 1659865, filed Oct. 12, 2016.

\* cited by examiner

CULTURE MEDIUM PREPARATOR COMPRISING A VESSEL PROVIDED WITH A CENTRAL STIRRER PUT INTO ROTATION BY A MAGNETIC RING

1. FIELD OF THE INVENTION

The invention relates to a device for maintaining a solution in a medium regulated in temperature by stirring it permanently. The invention applies more specifically to a device having a solution-preparing vessel provided with a stirrer rotationally driven by a magnetic mechanism.

2. BACKGROUND

In the industrial world, any commercially distributed item must meet prevailing standards. This is the case especially for food items to which stringent health standards apply. In the agro-food sector, these standards especially lay down maximum permissible quantities of microorganisms such as bacteria in a given volume of product. To verify the presence of these microorganisms and determine their quantity, it is common practice to take samples of foodstuffs and study the progress of microorganisms in a medium that greatly favors their proliferation.

To this end, samples of specific masses are removed from batches of products in order to produce samples that are then placed in Petri dishes. The Petri dish preliminarily contains a solution called agar that fosters the proliferation of this microorganisms when said dish is placed for a certain duration in a chamber regulated at a temperature and a pressure that are very precise. The dishes are opened at different points in time, typically over several days, and are subjected to tests to measure the density of the microorganisms present in the dish and its progress over time. If the density is below a certain threshold, then the batch from which the sample is extracted is considered to be fit for consumption.

The production of agar must be done in a sterile environment to obtain non-polluted samples. The production is done in temperature-regulated and pressure-re-regulated autoclaves. The chamber of the autoclave has a vessel provided with a dual sheathing that communicates cold or heat to the solution contained within it. However, this sheathing takes up a large portion in height of the vessel so that, if the quantity of the content is small and if this content is concentrated at the bottom of the vessel, then the coil heats/cools the walls unnecessarily, causing a lack of homogeneity of temperature.

To limit this problem, present-day autoclaves have a stirrer driven by a motor equipped with a magnetic system situated beneath the vessel. This stirrer is generally constituted by metal blades equipped with magnets in rotation about a shaft fixed to the bottom of the vessel. This layout causes an increase in the height of the apparatus to allow space for the mechanism for driving the stirrer beneath the vessel. In addition, mechanical and magnetic links situated beneath the vessel do not allow the bottom of the vessel to be heated or cooled by means of a heater element and a cooling device. Nor do they allow for a sample to be taken from the center of the culture medium through a tube. Cleaning is a delicate step because it is important to make the vessel perfectly clean and sterile before starting another production operation.

There is therefore a real need for a solution preparator, the vessel of which is easy to clean with a cloth to wipe the interior and a cleaning liquid that can be easily removed.

The present invention proposes a novel model of culture medium preparator that possesses a vessel having fewer uneven surfaces within it while at the same time being provided with a stirrer and an efficient sterilizing device.

4. SUMMARY OF THE INVENTION

An object of the invention especially is a culture medium preparator comprising a cylindrical vessel that terminates at the low part in a substantially hemispherical cap, a lid and a stirrer placed in the vessel. The stirrer comprises a vertical tube placed in the center of the vessel and a plurality of blades put into rotation about said tube and magnetic masses at the periphery so that they are placed in proximity to the internal wall of the vessel. The preparator furthermore comprises a magnetic ring in rotation about the internal wall at the same height as the magnetic masses, said magnets attracting said magnetic masses, the magnetic ring being moved in rotation by a motor.

In this way, the stirrer is driven in rotation without requiring mechanical elements placed inside the vessel, the absence of such elements facilitating the cleaning.

According to one particular embodiment, the culture medium preparator furthermore comprises a first heating cavity in contact with the internal wall, and around the cylindrical wall and a second heating cavity placed in contact with the internal wall and beneath the vessel, the magnetic ring being placed in the space left free between the two cavities. In this way, the mechanism for driving the stirrer is beneath the vessel thus enabling the heating means to be placed at this position, and the height of the apparatus is further limited.

According to another embodiment, each of the cavities comprises at least one inlet valve and one outlet valve enabling the creation of a current of fluid passing through said cavity. In this way, a current of fluid can be made to pass into these cavities in order to cool but also, if necessary, to heat the content of the tank more speedily.

According to another embodiment, the upper extremity of the tube of the stirrer passes through an orifice in the lid and the lower extremity of the tube slides into the interior of an insert situated at the center of the hemispherical cap, the orifice of the lid being situated vertically to the central axis of the vessel when the lid is lowered so as to center the upper part of the stirrer. In this way, in opening the lid, the elements of the stirrer are detached from the vessel and can be very easily removed for cleaning for example.

According to another embodiment, the substantially hemispherical cap is pierced at its center with a discharge hole, the lower extremity of the tube constituting a plug to block said hole. In this way, the discharging of the cleaning liquid is made easier.

According to another embodiment, the tube is hollow and open at both its extremities so as to extract the liquid content from the tank by suction. In this way, it is possible to aspirate the content of the vessel during the preparation without hampering the movement of the stirrer.

According to another embodiment, the culture medium preparator comprises a control unit controlling the temperature of heater elements placed in contact with the cavities, said control unit activating only the heater element placed in contact with the second cavity when the product placed inside the vessel does not exceed a determined height. In this way, the heating means can adapt to the quantity of liquid to be heated in the vessel.

5. BRIEF DESCRIPTION OF THE DRAWINGS

Figure 2:
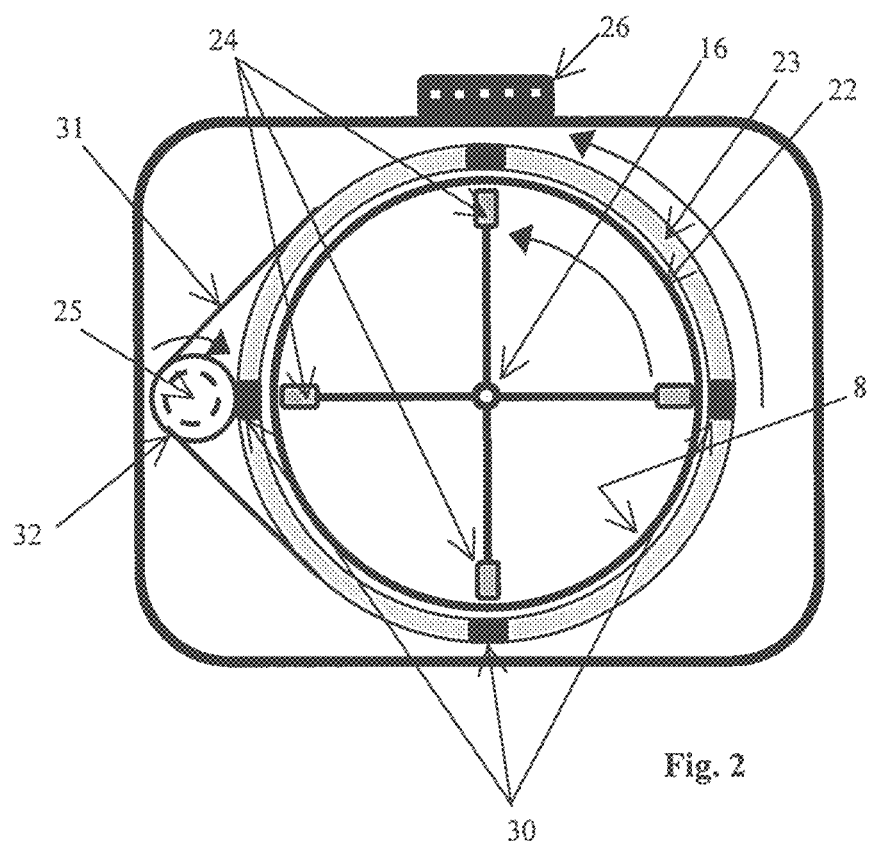
Figure 3:
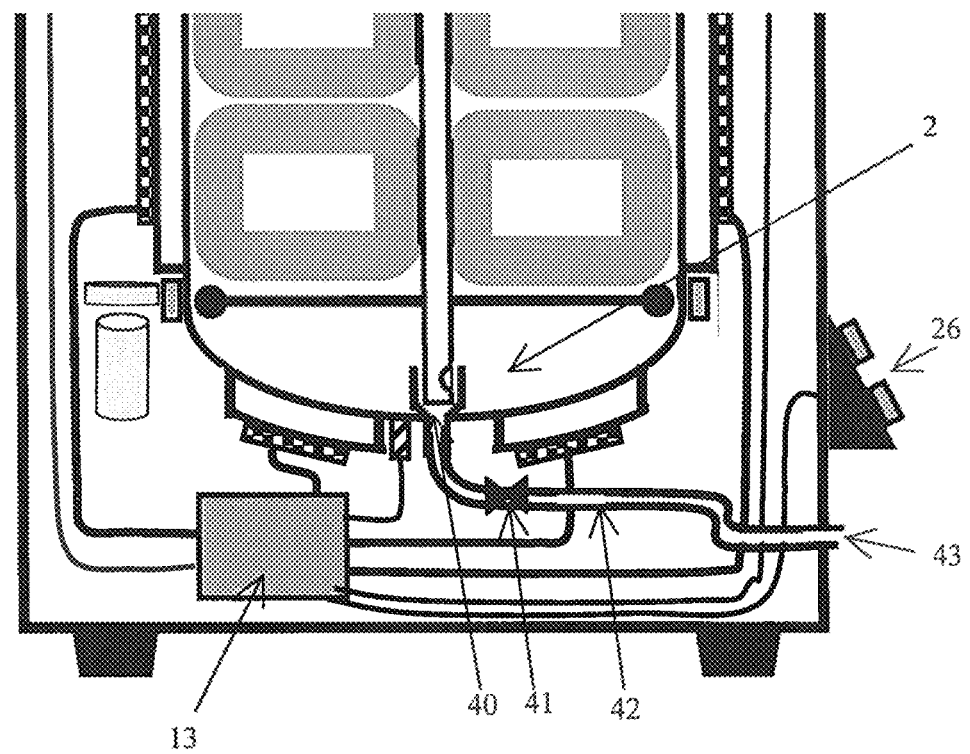
Figure 4:
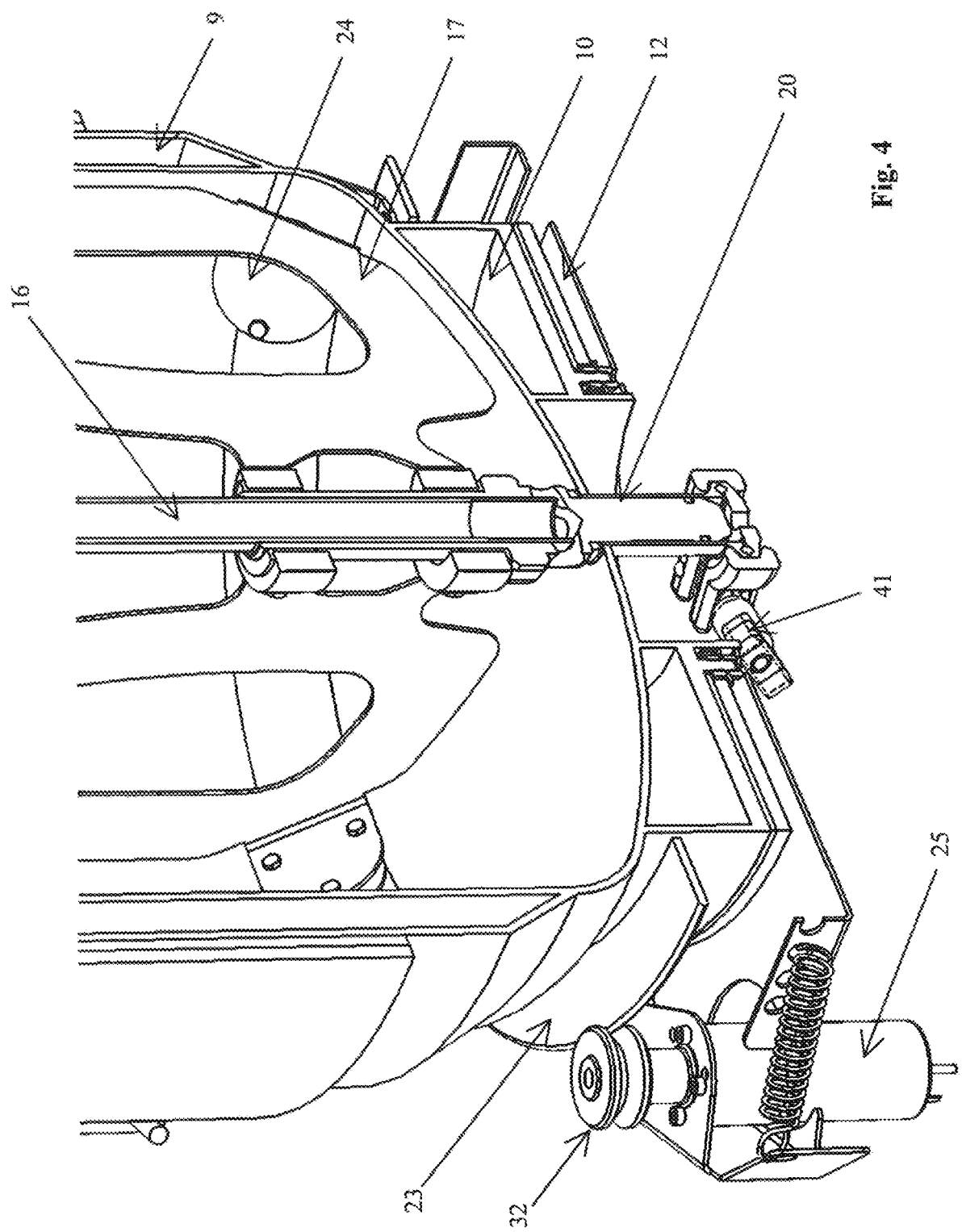
Figure 5:
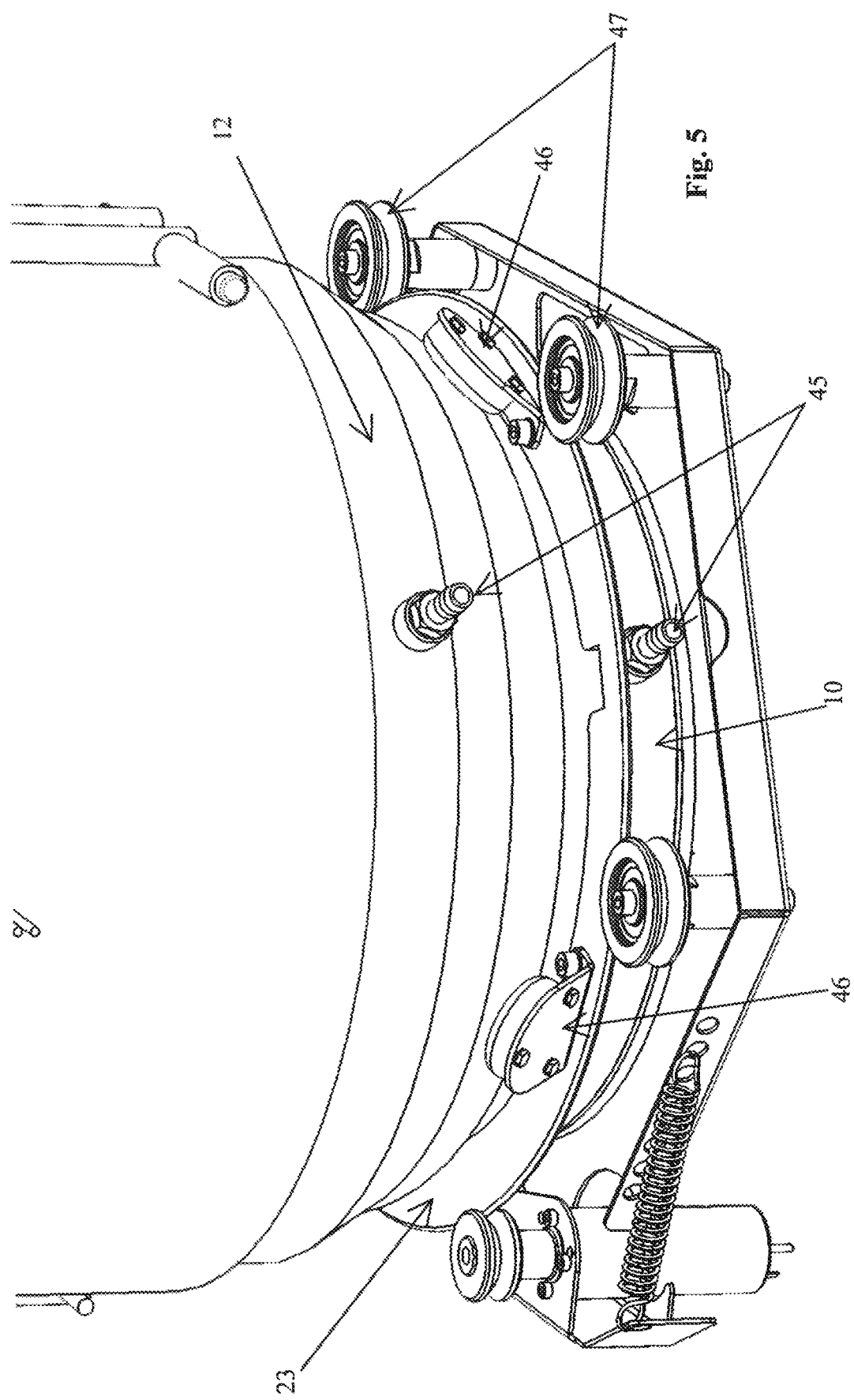
Figure 6:
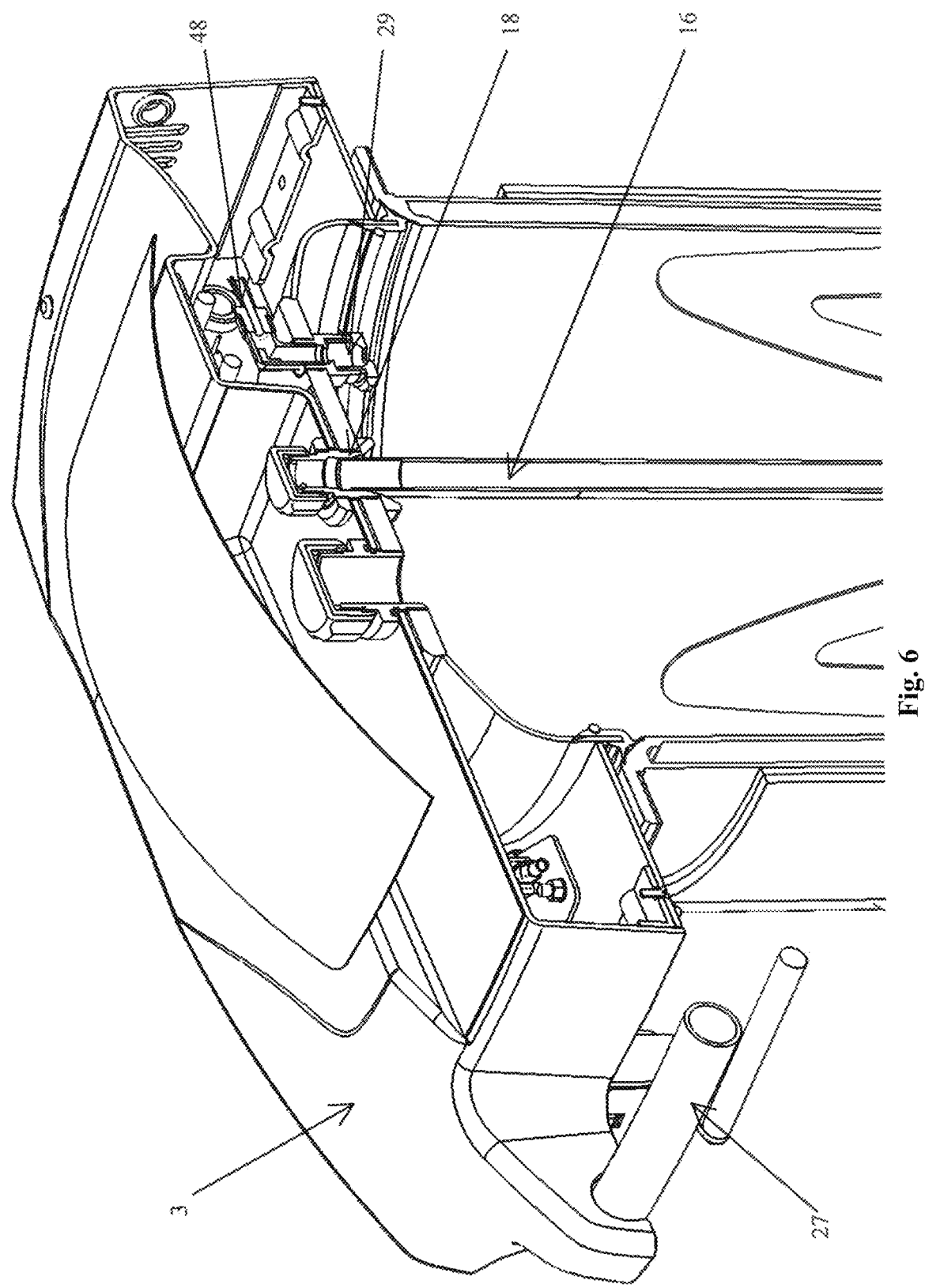

Other features and advantages of the invention shall now be seen in greater detail in the following description of exemplary embodiments given by way of a non-exhaustive illustration and with reference to the appended figures, of which:

FIG. 1 presents a view in vertical section of a culture medium preparator according to one exemplary embodiment of the invention;

FIG. 2 is a drawing seen from the top of the preparator of the stirrer driving ring according to one example of an embodiment, FIG. 3 presents a view in vertical section of the lower part of the preparator according to one improvement of the invention, FIG. 4 is a sectional drawing of a prototype culture medium preparator according to one exemplary embodiment of the invention, FIG. 5 is a drawing of the lower part of a prototype culture medium preparator according to one exemplary embodiment of the invention, FIG. 6 is a drawing of the upper part and of the lid of a prototype culture medium preparator according to one embodiment.

6. DETAILED DESCRIPTION

6.1 General Principle

The invention consists of a culture medium preparator comprising a cylindrical vessel that terminates at its lower part in a substantially hemispherical cap, a lid and a stirrer placed in the vessel. The stirrer comprises a vertical tube placed at the center of the vessel, a plurality of blades made to rotate about said tube and magnetic masses in periphery so that they are placed in proximity to the interior wall of the vessel. The preparator furthermore comprises a magnetic ring rotating about the internal wall at the same height as the magnetic masses, said magnets attracting said magnetic masses, the magnetic ring being driven in rotation by a motor. In this way, the stirrer is driven in rotation without requiring mechanical elements placed inside the vessel, the absence of such elements facilitating the cleaning operation.

6.2 Description of One Embodiment

FIG. 1 illustrates a culture medium preparator 1. This apparatus comprises a cylindrical vessel with a bottom in the form of a substantially hemispherical cap and having a circular aperture oriented upwards. The vessel 2, with a 30-litre capacity for example, is hermetically sealed by a pivoting lid 1 comprising at least two hinges 4 on one side and at least two bolts on the opposite side, the bolts being hooked to pins fixed to the framework of the apparatus. Once the vessel is closed, the interior can be put under pressure at 1 to 2 bars. Safety dictates that each bolt should be capable, independently of the other bolt, of keeping the vessel in a hermetically sealed position. The vessel is incorporated into a frame 6 placed on feet 7.

The sheathing of the vessel 2, made for example out of stainless steel, is constituted by an internal wall 8 and an external wall 8'. The vessel is cylindrical with a substantially spherical bottom. The external wall 8' is interrupted at the lower part of the cylindrical side and resumes so that it covers a part of the bottom of the vessel, in forming a substantially hemispherical and hollow plate. The dual sheathing of the vessel thus forms two cavities, one cavity 9 at the upper part and the other cavity 10 at the bottom of the vessel, these cavities being designed to contain a liquid, for example water from the mains system. Once the cavities are filled, the dual sheathing 8 and 8' is isolated by the closing of inlet and outlet solenoid valves (not shown in FIG. 1).

The vessel has two heating means, the first heating means being positioned about the external wall 8' in contact with the cavity 9 while the second heating means is placed beneath the vessel in contact with the external wall 8' of the cavity 10. According to one preferred exemplary embodiment, these heating means are formed by electrical resistors. It can be noted that the resistor at the bottom of this vessel is the most efficient means to obtain a rapid rise in temperature. A control unit 13 controls the temperature of the liquid. The rise in temperature of the content of the vessel is obtained by contact with the internal wall 8.

According to one improvement, several sensors 14 are placed in contact with the internal wall of the vessel in order to measure the temperature at this place, one being placed at the top of the vessel and another at the bottom of the vessel. The sensors 14 are connected to the control unit 13 which, depending on the values measured, controls the rise and fall of the temperature of the heat-carrying liquid flowing in the lower cavity 10 and/or the upper cavity 9.

A vertical stirrer 15 is placed at the center of the vessel. It has a vertical shaft constituted by a hollow straight tube 16, having a diameter of preferably 17 to 18 centimeters, and open at both extremities. The stirrer also has the plurality of blades 17 forming perforated vertical surfaces grouped together in several vertical planes, for example two planes extending axially relative to the tube 16 and intersecting at right angles. The blades are fixedly attached to each other and constitute a monobloc unit that rotates about the shaft by means of at least two blades placed at the top and at the bottom. Each group of blades on a radius possesses its symmetrical counterpart on the other side of the vertical shaft. In this way the stirrer is balanced and its center of gravity is situated on the central shaft of the straight tube 16. The straight tube passes through the lid 3 by a circular orifice 18 that is situated vertically to the central shaft of the vessel when the lid is lowered. In this way, the stirrer is centered vertically in the middle of the vessel 2. The width of the stirrer defined by the groups of blades is smaller than the internal diameter of the vessel by some millimeters. In this way, the blades of the stirrer brush against the walls of the vessel and ensure a homogenous mixture in mixing the constituent elements and enabling a homogenous temperature. When the operator closes the lid, the upper extremity of the tube 16 naturally comes out through the orifice 18. The lower section of this orifice is truncated cone and narrows towards the top to improve the centering and prevent the external ridges of the blades 17 from touching the internal walls of the vessel.

The base of the tube is engaged in a hollow insert 20 that can be dismantled, opened with four cylindrical holes at its base. These holes enable the exit of the liquid contained in the vessel through at least one hole 21 made at the very bottom of the hollow tube 16. This arrangement enables the suction of the content of the vessel so that this content reaches a very low level, thus reducing the dead volume of the vessel to a minimum value. The insert 20 is itself engaged in the drain hole of the vessel which maintains it in the vertical position, in the axis of the vessel, without any clearance. This is achieved by means of an O-ring seal which cancels out the clearance. This insert is equipped with a lip seal at its widest part, in contact with the vessel, thus ensuring perfect sealing through pressure from the stirrer. In this way, and according to a preferred embodiment, the extremity of the tube serves as a plug and the fact of removing it enables the content to flow away through a pipe (not shown in FIG. 1). In this way, the cleaning is done with large quantities of water, the fouled liquid flowing by gravity through a discharge orifice situated in the lowest part of the vessel.

The insert therefore comprises several advantages in being used as a:
  draining plug,
  rotation shaft for the stirrer,
  guide for the sample-taking tube,
  sample-taking nozzle of the tube.

This arrangement prevents the discharge hole from being closed by means of a valve shifted to a position beneath the vessel or outside the vessel, thus leading to the presence of a volume in a pipe that cannot be heated by the electrical resistors and therefore cannot be effectively sterilized. The fact of placing the insert used as a plug at the bottom of the vessel ensures the sterilization of the entire volume of the vessel because the insert used as a plug is itself put under temperature of 121° C.

As can be seen in FIG. 1, the stirrer 12 is driven rotationally about its vertical axis and is centered at the middle of the vessel by the insert 16 at the lower part and the orifice 15 in the lid.

The extraction of the liquid content can be done by a hole 17 made at the bottom of the tube 13. The upper extremity of the tube is connected by a tight-sealing rotary seal to a pipe, itself connected to a pump (not shown in FIG. 1). The pump generates a vacuum in the pipe which sucks out the content and pours it into receptacles such as Petri dishes for example. The fact of using the tube at the center of the stirrer as a means for extracting the content of the vessel averts the need for having outlet plugs for the vessel which could get fouled and which, in any case, would be difficult to clean. The cleaning of the tube is facilitated by the fact that it is simply threaded into the insert. It is sufficient therefore to exert a simple vertical traction force to remove it from the vessel. The dismantling of the stirrer device and of the insert is done in the same way, after the tube has been removed.

As can be seen in FIG. 1, the cavities 9 and 10 are separated by a space in the form of a hemispherical ring. The tank in contact with this space is devoid of any external wall 8. The space is put to good use, the mechanism for driving the stirrer 15 in rotation being fitted therein.

According to a preferred embodiment, the space 22 situated between the cavities 9 and 10 comprises a ring 23 capable of rotating about the bottom part of the vessel. The ring has a plurality of magnets disposed at regular intervals. The magnets attract an equal number of magnetic masses 24 placed at the extremity of the blades at the same height as the ring 23 and disposed radially relative to the straight tube 13. The geometry of the positioning of the magnets and of the magnetic masses of the stirring device is designed so that these elements are situated at a minimum distance in being separated by an internal wall of the vessel. The magnetic masses 24 can also be formed by the blades themselves, which will then be metallic. Small rollers equipped with ball bearings are placed in the space at the bottom of the groove 16 and facilitate the rotation of the ring. A motor 25 commanded by the control unit 13 drives a belt in rotation. The belt surrounds the ring and drives its motion. The rotation of the ring drives that of the stirrer, the speed of rotation depending on that of the motor 19. The magnetic coupling averts the need for piercing the vessel for the passage of a drive shaft, thus making it easier to clean. The cylindrical shape of the vessel, with a substantially hemispherical bottom, and the fact that there are no uneven features that would hamper the passage of a sponge or cloth also contribute to easy cleaning.

According to one alternative embodiment, the motor 25 drives a friction wheel which is in contact with the external surface of the ring 23.

The fact that the mechanism for driving the stirrer in rotation is situated beneath and at the periphery of the bottom of the vessel has the advantage of providing free space to place the heating means 12 therein along with a discharge orifice at the bottom of the vessel.

The settings of the apparatus are introduced by a man-machine interface (MMI) which can take the form of a keypad 26 with buttons and display units or in the form of a touchpad. Acquisition by voice with a voice recognition engine is also possible as a means of acquiring commands. The MMI has a buzzer or a loudspeaker to emit sounds, especially alarm signals.

The lid 3 is solidly closed by means of bolts 5 which get inserted into grooves forming a fixed part of the frame. The bolts extend upwards into a grip 27, the entire unit pivoting about a horizontal axis. A sensor 28 permanently checks the position of the bolt and interrupts the rotation of the stirrer immediately when the grip is handled. Advantageously, a magnetic bolt blocks the opening in the closed position so long as the stirrer is moving.

According to one improvement, the lid has a communications valve 29 for communications with the exterior of the apparatus. This valve enables especially the inlet of air into the vessel after passage through a filter. This inlet is protected by a particle filter upstream (a carded cotton trap) and by a 0.2 µM disk filter downstream, so as to prevent any contamination of the prepared medium, through this solenoid valve. The valve 29 is open at the end of the preparation of the content in order to balance pressure before opening the lid.

FIG. 2 presents a horizontal section of the culture medium preparator 1 at the space 22 left free between the two heating cavities 9 and 10. The free space which extends in depth up to the internal sheathing of the vessel 8 comprises a circular ring 23 designed to rotate inside the free space 22 at the closest possible distance from the internal sheathing of the vessel 8. Small rollers ensure the guidance in rotation of the circular ring 23. The ring 23 has magnets 30 at regular intervals. There are four magnets (this number being given by way of an example) in FIG. 2. Each magnet is placed relative to its neighboring magnets so that they rotate at 90° relative to each other. The magnets 30 attract an equal number of magnetic masses 24 placed at the periphery of the stirrer, as close as possible to the internal sheathing 8. The angular distances between the magnetic masses are equal to those of magnets 22 of the ring 17 so that the stirrer rotates naturally to reduce the distance between the masses and the magnets. The mechanical characteristics of the magnets 22 and of the masses are chosen so that the magnetic forces perfectly balance out, thus enabling the stirrer to be held in a strictly vertical position during rotation, its axis coinciding with the central axis of the vessel.

The ring is driven in rotation by a belt 31, itself driven by a friction wheel 32 fixed to the shaft of a motor 25 (seen in a sectional view in FIG. 2). The rotation of the ring 23 driving the rotation of the stirrer according to an angular speed controlled by the control unit 13. The position of the means for driving the stirrer, situated around the vessel and not beneath it, reduces the height of the apparatus.

The control unit 13 receives commands introduced at the MMI 26. The operator enters the quantity of product in liquid state in terms of volume and, on the basis of this volume, the control unit determines the height of product in the vessel 2. If this height does not exceed a determined height ranging from ¼ to ¾ of the total height of the vessel, the resistor 11 surrounding the vessel is not used and the control unit controls the temperature by using only the resistor 12 at the bottom of the vessel. In this way, energy is saved since only one heating means is used and the control is not exerted on the zones that do not contain any product, thus preventing the formation of hot or cold spots and fostering improved homogeneity of temperature.

According to one improvement illustrated in FIG. 3, the bottom of the vessel 3 comprises a discharge orifice 40 in its lowest part. This orifice is extended by a pipe 42 and a manual valve 41. The pipe 42 is extended after the solenoid valve and passes through the frame to exit on the exterior by a mouth 43. According to one alternative embodiment, the solenoid valve 41 can be controlled by the control unit 13 and the MMI 26 for example in the context of an automatic cleaning cycle.

According to one example of operation, the content of the vessel is taken to 121° C. for a duration of 15 minutes and then to 47° C. which is the temperature just above the freezing limit. This drop in temperature is accelerated by opening an inlet valve and an outlet valve for each cavity 9 and 10 and injecting cold water coming from the mains (or possibly from a refrigeration unit) to create a current of liquid in the cavity of the wall of the vessel and thus cool the content.

FIG. 4 presents a sectional drawing of a prototype culture medium preparator according to one embodiment. This drawing shows especially the cavity 9 surrounding the bottom of the vessel and the cavity 10 situated beneath the bottom of the vessel, the electrical resistor 12 in contact with the cavity 10, the blades 17 of the stirrer situated symmetrically about the hollow shaft 13 centered at the lower part by the insert 20, the motor 25 and the pulley 32 rotationally driving the magnetic ring 23. The insert ends at the lower part in a liquid outlet closed by a manual valve 41.

FIG. 5 presents a drawing of the lower part of a prototype of a culture medium preparator according to one embodiment. In addition to the above figure, this figure shows the position of the inlet and outlet valves 25 for liquid present in the cavities 9 and 10. Pipes are connected to these valves to convey a temperature-regulated liquid or simply water coming from the mains to rapidly cool the content of the apparatus. This figure also shows magnets 26 mounted on the magnetic ring 23 as well as rollers 27 guiding the rotation of this ring. In this figure, the magnetic ring is driven by direct friction on a pulley mounted on the motor.

FIG. 6 presents a drawing of the upper part and of the lid 3 of a prototype of a culture medium preparator according to one embodiment. This drawing especially shows the orifice 18 for the passage of the hollow tube 16 of the stirrer as well as the communications valve 29 enabling the interior of the vessel to communicate with the ambient air. This valve is extended towards the right of the figure by the filter 28.

Although the present invention has been described with reference to the particular embodiments illustrated, it is no way limited by these embodiments, being limited only by the scope of the claims appended here below. It can be noted that changes or modifications could be made by those skilled in the art.

The invention claimed is:

1. A culture medium preparator comprising:
   a cylindrical vessel that terminates at a low part in a substantially hemispherical cap;
   a lid;
   a stirrer placed in the vessel, said stirrer comprising a vertical tube placed in a center of the vessel and a plurality of blades put into rotation about said tube; wherein the stirrer comprises magnetic masses at a periphery so that they are placed in proximity to an internal wall of the vessel;
   a magnetic ring in rotation about the internal wall at a same height as the magnetic masses, said magnets attracting said magnetic masses, the magnetic ring being movable in rotation by a motor; and
   at least one heater element positioned to heat at least one of the wall or a bottom of the vessel to regulate a temperature of content in the vessel,
   the vertical tube being hollow and open at both its extremities so as to extract liquid content from the bottom of vessel by suction.

2. The culture medium preparator according to claim 1, wherein the preparator furthermore comprises a first heating cavity in contact with the internal wall, and around the cylindrical wall and a second heating cavity placed in contact with the internal wall and beneath the vessel, the magnetic ring being placed in a space left free between the two cavities.

3. The culture medium preparator according to claim 2, wherein each of the first and second heating cavities comprises at least one inlet valve and one outlet valve enabling creation of a current of fluid passing through said cavity.

4. The culture medium preparator according to claim 2, wherein the at least one heater element comprises a first heater element placed in contact with the first heating cavity and a second heater element placed in contact with the second heating cavity, and wherein the preparator comprises a control unit controlling a temperature of the first and second heater elements, said control unit activating only the second heater element placed in contact with the second cavity when a product placed inside the vessel does not exceed a determined height.

5. The culture medium preparator according to claim 1, wherein an upper extremity of the tube of the stirrer passes through an orifice in the lid and a lower extremity of the tube slides into the interior of an insert situated at the center of the hemispherical cap, the orifice of the lid being situated vertically to a central axis of the vessel when the lid is lowered so as to center an upper part of the stirrer.

6. The culture medium preparator according to claim 5, wherein the substantially hemispherical cap is pierced at its center with a discharge hole, the lower extremity of the tube constituting a plug to block said hole.

\* \* \* \* \*